United States Patent
Karasawa

(10) Patent No.: US 11,927,703 B2
(45) Date of Patent: Mar. 12, 2024

(54) ULTRASOUND SYSTEM AND METHOD FOR CONTROLLING ULTRASOUND SYSTEM

(71) Applicant: FUJIFILM Corporation, Tokyo (JP)

(72) Inventor: Hiroyuki Karasawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 681 days.

(21) Appl. No.: 17/093,415

(22) Filed: Nov. 9, 2020

(65) Prior Publication Data
US 2021/0055396 A1 Feb. 25, 2021

Related U.S. Application Data

(63) Continuation of application No. PCT/JP2019/018389, filed on May 8, 2019.

(30) Foreign Application Priority Data

May 18, 2018 (JP) .................................. 2018-096508

(51) Int. Cl.
  *G01S 7/52* (2006.01)
  *G01S 15/89* (2006.01)
  (Continued)

(52) U.S. Cl.
  CPC ...... *G01S 7/52053* (2013.01); *G01S 15/8934* (2013.01); *G01S 15/8993* (2013.01);
  (Continued)

(58) Field of Classification Search
  CPC . G01S 7/52053; G06F 3/0488; H04B 1/3827; H04B 11/00; H04N 7/183
  See application file for complete search history.

(56) References Cited

U.S. PATENT DOCUMENTS

2014/0350357 A1* 11/2014 Lee .................. A61B 8/4477
                                                             600/443
2015/0121277 A1* 4/2015 Yoon ................. G06F 3/04845
                                                             715/771
(Continued)

FOREIGN PATENT DOCUMENTS

CN       106923863 A    7/2017
JP       2014115733 A   6/2014
(Continued)

OTHER PUBLICATIONS

The Japan Society of Ultrasonics in Medicine; "Data on the safety of ultrasonic diagnostic equipment"; 3rd edition; Apr. 2014; pp. 1-44; URL: https//www.jsum.or.jp/committee/uesc/pdf/safty.pdf.

(Continued)

*Primary Examiner* — Dixomara Vargas
(74) *Attorney, Agent, or Firm* — Studebaker & Brackett PC

(57) ABSTRACT

In an ultrasound system 1, a mobile information terminal 3 is wirelessly connected to an ultrasound probe 2 and an external monitor 4. The ultrasound probe 2 includes: a transducer array 11; a transmitting and receiving unit 14 that generates a sound ray signal by directing the transducer array 11 to transmit and receive ultrasonic waves; and an image information data generation unit 19 that generates image information data from the sound ray signal. The mobile information terminal 3 includes: a display unit 34; an operation unit 39 including a touch sensor; an operation image generation unit 37 that generates an operation image for an input operation; an external monitor data generation unit 36 that generates external monitor data from the image information data; and a terminal-side wireless communication unit 32 that transmits the external monitor data to the external monitor 4. The external monitor 4 displays an (Continued)

external monitor ultrasound image based on the external monitor data.

12 Claims, 6 Drawing Sheets

(51) Int. Cl.
    *H04B 1/3827*    (2015.01)
    *H04B 11/00*     (2006.01)
    *H04N 7/18*      (2006.01)
    *A61B 8/00*      (2006.01)
    *A61B 8/08*      (2006.01)
    *A61B 8/14*      (2006.01)
    *G06F 3/0488*    (2022.01)

(52) U.S. Cl.
    CPC ........... *H04B 1/3827* (2013.01); *H04B 11/00* (2013.01); *H04N 7/183* (2013.01); *A61B 8/14* (2013.01); *A61B 8/4472* (2013.01); *A61B 8/465* (2013.01); *A61B 8/467* (2013.01); *A61B 8/5207* (2013.01); *A61B 8/54* (2013.01); *G06F 3/0488* (2013.01)

(56) References Cited

U.S. PATENT DOCUMENTS

| | | | |
|---|---|---|---|
| 2015/0164481 A1* | 6/2015 | Lee | G06T 15/08 600/440 |
| 2015/0190119 A1* | 7/2015 | Park | A61B 8/5223 600/440 |
| 2015/0209011 A1* | 7/2015 | Lee | A61B 8/463 600/441 |
| 2015/0245823 A1* | 9/2015 | Jin | A61B 8/14 600/443 |
| 2015/0272543 A1* | 10/2015 | Kim | A61B 8/461 600/437 |
| 2015/0302604 A1* | 10/2015 | Lee | G06T 19/00 345/424 |
| 2016/0058410 A1* | 3/2016 | Kim | A61B 8/5246 600/437 |
| 2016/0085328 A1* | 3/2016 | Lee | G16H 50/20 345/173 |
| 2016/0106394 A1* | 4/2016 | Kang | A61B 8/465 600/437 |
| 2016/0120506 A1* | 5/2016 | Lee | A61B 8/5207 600/437 |
| 2016/0151041 A1* | 6/2016 | Lee | A61B 8/5207 600/440 |
| 2016/0157824 A1* | 6/2016 | Park | A61B 8/463 600/437 |
| 2016/0183925 A1* | 6/2016 | Kim | A61B 8/463 600/440 |
| 2016/0199022 A1* | 7/2016 | Kim | A61B 8/5223 600/454 |
| 2016/0220231 A1* | 8/2016 | Lee | A61B 8/5207 |
| 2016/0350503 A1* | 12/2016 | Jun | A61B 8/465 |
| 2017/0011509 A1* | 1/2017 | Ryu | A61B 8/5261 |
| 2017/0100098 A1 | 4/2017 | Urabe et al. | |
| 2018/0064416 A1* | 3/2018 | Gu | A61B 8/429 |
| 2018/0271495 A1* | 9/2018 | Lee | A61B 8/5207 |
| 2019/0038260 A1 | 2/2019 | Lee et al. | |
| 2019/0090846 A1* | 3/2019 | Lee | A61B 8/4405 |
| 2019/0125294 A1* | 5/2019 | Hyun | A61B 8/488 |
| 2020/0323514 A1* | 10/2020 | Thienphrapa | A61B 8/5223 |
| 2021/0298720 A1* | 9/2021 | Karasawa | G06F 3/14 |
| 2022/0117579 A1* | 4/2022 | Hattori | A61B 8/4483 |
| 2022/0125409 A1* | 4/2022 | Hattori | A61B 8/4494 |
| 2022/0142616 A1* | 5/2022 | Murakami | A61B 8/469 |
| 2022/0147974 A1* | 5/2022 | Law | H04L 9/3239 |
| 2023/0103571 A1* | 4/2023 | Yamamoto | A61B 8/4245 600/437 |
| 2023/0108655 A1* | 4/2023 | Yamamoto | A61B 8/463 600/437 |

FOREIGN PATENT DOCUMENTS

| | | |
|---|---|---|
| JP | 2015197694 A | 11/2015 |
| JP | 2017086360 A | 5/2017 |
| JP | 2017153584 A | 9/2017 |
| WO | 2017/135769 A1 | 8/2017 |

OTHER PUBLICATIONS

International Search Report issued in PCT/JP2019/018389; dated Jun. 4, 2019.

International Preliminary Report on Patentability and Written Opinion issued in PCT/JP2019/018389; dated Nov. 24, 2020.

The extended European search report issued by the European Patent Office dated May 26, 2021, which corresponds to European Patent Application No. 19804172.5-1126 and is related to U.S. Appl. No. 17/093,415.

An Office Action; "Notice of Reasons for Refusal", mailed by the Japanese Patent Office dated Dec. 14, 2021, which corresponds to Japanese Patent Application No. 2020-519584 and is related to U.S. Appl. No. 17/093,415; with English language translation.

An Office Action; "Decision of Refusal", mailed by the Japanese Patent Office dated Jun. 14, 2022, which corresponds to Japanese Patent Application No. 2020-519584 and is related to U.S. Appl. No. 17/093,415 with English language translation.

An Office Action mailed by China National Intellectual Property Administration dated Oct. 31, 2023, which corresponds to Chinese U.S. Appl. No. 17/093,415.5 and is related to U.S. Appl. No. 17/093,415; with English language translation.

\* cited by examiner

ULTRASOUND SYSTEM AND METHOD FOR CONTROLLING ULTRASOUND SYSTEM

CROSS-REFERENCE TO RELATED APPLICATIONS

This application is a Continuation of PCT International Application No. PCT/JP2019/018389 filed on May 8, 2019, which claims priority under 35 U.S.C. § 119(a) to Japanese Patent Application No. 2018-096508 filed on May 18, 2018. The above application is hereby expressly incorporated by reference, in its entirety, into the present application.

BACKGROUND OF THE INVENTION

1. Field of the Invention

The present invention relates to an ultrasound system and a method for controlling the ultrasound system, and more particularly, to an ultrasound system that displays an ultrasound image on an external monitor and a method for controlling the ultrasound system.

2. Description of the Related Art

In the related art, an ultrasound diagnostic apparatus using an ultrasound image has been put to practical use in the medical field. In general, this type of ultrasound diagnostic apparatus includes an ultrasound probe having a transducer array provided therein and an apparatus main body connected to the ultrasound probe. Ultrasonic waves are transmitted from the ultrasound probe to a subject. The ultrasound probe receives ultrasound echoes from the subject. The apparatus main body electrically processes a reception signal to generate an ultrasound image.

In recent years, for example, as disclosed in JP2017-086360A, an ultrasound system has been developed which displays an ultrasound image acquired by an ultrasound probe on an external monitor disposed at a position away from a user and comprises a mobile information terminal for performing an input operation on the ultrasound probe and the external monitor, which makes it possible to improve convenience in ultrasound diagnosis.

SUMMARY OF THE INVENTION

However, in the ultrasound system disclosed in JP2017-086360A, the external monitor performs a process for generating an ultrasound image, and the mobile information terminal generates an image used to operate the ultrasound system on the basis of the data generated by the external monitor. As such, in the ultrasound system disclosed in JP2017-086360A, the process performed in the mobile information terminal is complicated and there is room for further improvement in the method of generating and displaying the image for the user in the mobile information terminal.

The invention has been made in order to solve the problems of the related art and an object of the invention is to provide an ultrasound system and a method for controlling the ultrasound system that can improve convenience in ultrasound diagnosis while facilitating the observation of an ultrasound image and an input operation for ultrasound diagnosis.

In order to achieve the above object, according to the invention, there is provided an ultrasound system in which a mobile information terminal is connected to an ultrasound probe and an external monitor. The ultrasound probe includes: a transducer array; a transmitting and receiving unit that transmits ultrasonic waves from the transducer array and generates a sound ray signal on the basis of a reception signal acquired by the transducer array; an image information data generation unit that generates image information data on the basis of the sound ray signal generated by the transmitting and receiving unit; and a probe-side wireless communication unit that wirelessly transmits the image information data to the mobile information terminal. The mobile information terminal includes: a display unit; an operation unit that includes a touch sensor disposed so as to be superimposed on the display unit and is used by a user to perform an input operation; an operation image generation unit that generates an operation image which is displayed on the display unit and is used by the user to perform the input operation through the touch sensor; an external monitor data generation unit that generates external monitor data having a display format for the external monitor on the basis of the image information data wirelessly transmitted from the ultrasound probe; and a terminal-side wireless communication unit that wirelessly transmits the external monitor data generated by the external monitor data generation unit to the external monitor. The external monitor displays an external monitor ultrasound image on the basis of the external monitor data wirelessly transmitted from the mobile information terminal.

In a case in which the external monitor ultrasound image is not displayed on the external monitor, the display unit may display the operation image and a terminal ultrasound image based on the image information data generated by the image information data generation unit.

Further, the external monitor data may include data corresponding to the external monitor ultrasound image and the operation image generated by the operation image generation unit, and the external monitor may display the external monitor ultrasound image and an external monitor operation image that is the same as the operation image displayed on the display unit of the mobile information terminal on the basis of the external monitor data.

Furthermore, preferably, the external monitor has an external-monitor-side display screen having a first size, the display unit of the mobile information terminal has a terminal-side display screen having a second size that is smaller than the first size, the external monitor operation image has a size equal to the second size of the terminal-side display screen, and the external monitor ultrasound image has a third size that is smaller than the first size and is larger than the second size.

Preferably, a wireless communication method between the mobile information terminal and the ultrasound probe is different from a wireless communication method between the mobile information terminal and the external monitor.

For example, preferably, a frequency band in wireless communication between the mobile information terminal and the ultrasound probe is different from a frequency band in wireless communication between the mobile information terminal and the external monitor.

Further, the mobile information terminal may include a safety evaluation index calculation unit that calculates a safety evaluation index on the basis of ultrasound transmission and reception conditions controlled by an ultrasound transmission and reception control unit of the ultrasound probe and displays the safety evaluation index on the display unit.

Preferably, the image information data is a signal obtained by performing attenuation correction according to a depth of a reflection position of the ultrasonic waves and an envelope detection process on the sound ray signal generated by the transmitting and receiving unit.

Alternatively, the image information data may be an ultrasound image signal obtained by performing attenuation correction according to a reflection position of the ultrasonic waves and an envelope detection process on the sound ray signal generated by the transmitting and receiving unit and converting the sound ray signal according to a predetermined image display method.

Preferably, the transmitting and receiving unit includes: a transmitting unit that directs the transducer array to transmit the ultrasonic waves; and a receiving unit that generates the sound ray signal on the basis of the reception signal acquired by the transducer array.

According to the invention, there is provided a method for controlling an ultrasound system in which a mobile information terminal is connected to an ultrasound probe and an external monitor. The method comprises: generating a sound ray signal by directing a transducer array of the ultrasound probe to transmit and receive ultrasonic waves on the basis of an input operation through an operation unit of the mobile information terminal; generating image information data on the basis of the generated sound ray signal; wirelessly transmitting the generated image information data from the ultrasound probe to the mobile information terminal; generating an operation image used by a user to perform the input operation; displaying the operation image on a display unit; generating external monitor data having a display format for the external monitor on the basis of the image information data wirelessly transmitted from the ultrasound probe; wirelessly transmitting the generated external monitor data from the mobile information terminal to the external monitor; and displaying an external monitor ultrasound image on the external monitor on the basis of the external monitor data.

According to the invention, the mobile information terminal includes: the display unit; the operation unit that includes the touch sensor disposed so as to be superimposed on the display unit and is used by the user to perform the input operation; the operation image generation unit that generates the operation image which is displayed on the display unit and is used by the user to perform the input operation through the touch sensor; the external monitor data generation unit that generates the external monitor data having the display format for the external monitor on the basis of the image information data wirelessly transmitted from the ultrasound probe; and the terminal-side wireless communication unit that wirelessly transmits the external monitor data generated by the external monitor data generation unit to the external monitor. The external monitor displays the external monitor ultrasound image on the basis of the external monitor data wirelessly transmitted from the mobile information terminal. Therefore, it is possible to improve convenience while facilitating the observation of an ultrasound image and an input operation for ultrasound diagnosis.

DESCRIPTION OF THE PREFERRED EMBODIMENTS

Embodiments of the invention will be described below with reference to the accompanying drawings.

Embodiment 1

Figure 1:
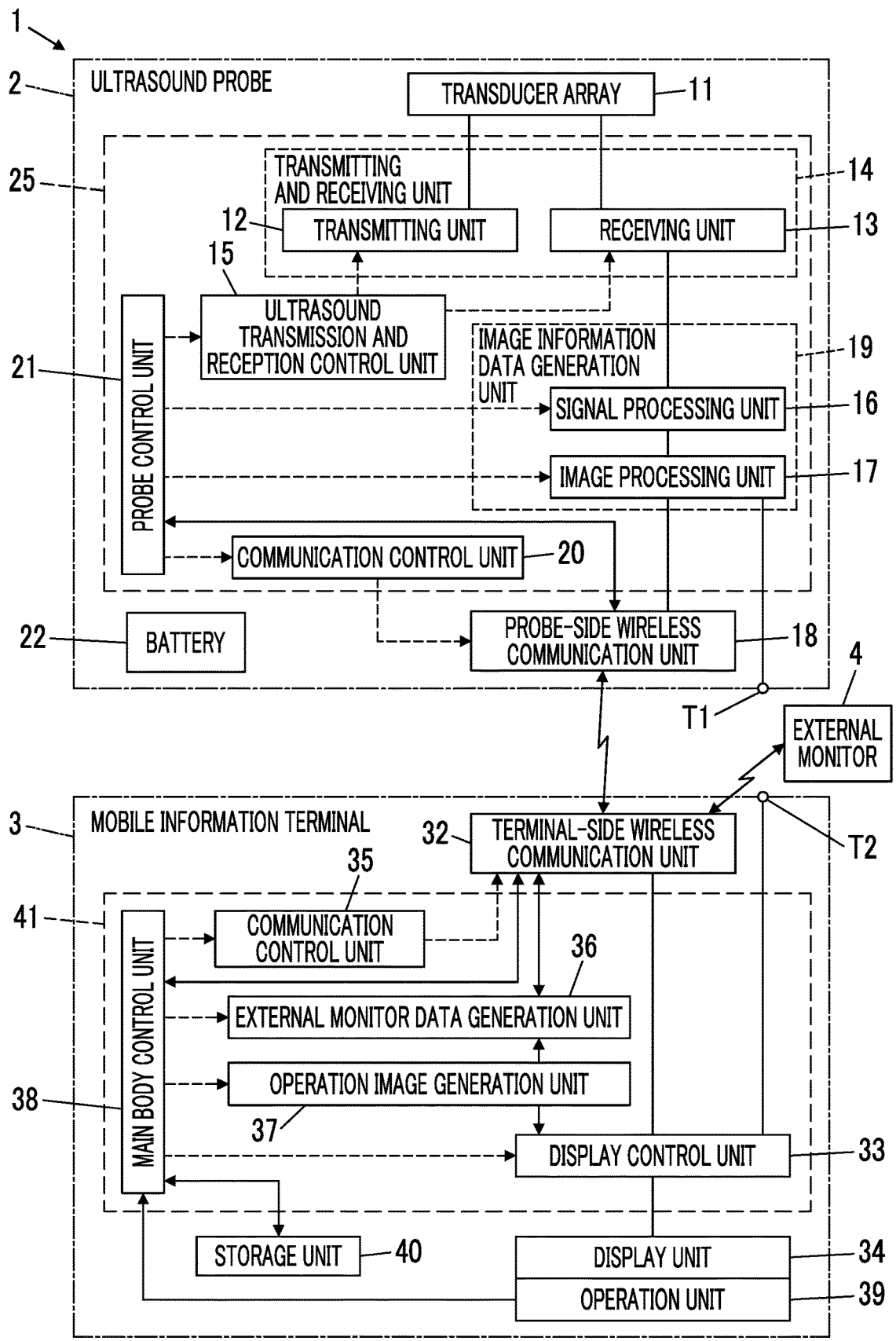
FIG. 1 is a block diagram illustrating a configuration of an ultrasound system according to Embodiment 1 of the invention.

FIG. 1 illustrates the configuration of an ultrasound system 1 according to Embodiment 1 of the invention. The ultrasound system 1 comprises an ultrasound probe 2, a mobile information terminal 3, and an external monitor 4. The ultrasound probe 2 and the mobile information terminal 3 are connected to each other by wireless communication. The mobile information terminal 3 and the external monitor 4 are connected to each other by wireless communication.

The ultrasound probe 2 comprises a transducer array 11. The transducer array 11 is connected to a transmitting unit 12 and a receiving unit 13. The transmitting unit 12 and the receiving unit 13 form a transmitting and receiving unit 14. An ultrasound transmission and reception control unit 15 is connected to the transmitting unit 12 and the receiving unit 13. The signal processing unit 16 and the image processing unit 17 are connected to the receiving unit 13. Here, an image information data generation unit 19 is configured by the signal processing unit 16 and the image processing unit 17. Further, a probe-side wireless communication unit 18 and a probe-side connection terminal T1 are connected to the image processing unit 17, and a communication control unit 20 is connected to the probe-side wireless communication unit 18.

A probe control unit 21 is connected to the ultrasound transmission and reception control unit 15, the signal processing unit 16, the image processing unit 17, the probe-side wireless communication unit 18, and the communication control unit 20. Here, the probe-side wireless communication unit 18 and the probe control unit 21 are connected such that information can be bidirectionally transmitted and received. Further, the ultrasound probe 2 has a battery 22 provided therein.

In addition, a probe-side processor 25 is configured by the transmitting and receiving unit 14, the ultrasound transmission and reception control unit 15, the image information data generation unit 19, the communication control unit 20, and the probe control unit 21.

The mobile information terminal 3 has a terminal-side wireless communication unit 32. A display control unit 33 is connected to the terminal-side wireless communication unit 32. A communication control unit 35 and an external monitor data generation unit 36 are connected to the terminal-side wireless communication unit 32. The terminal-side wireless communication unit 32 and the external monitor data generation unit 36 are connected such that information can be bidirectionally transmitted and received. Further, an operation image generation unit 37 is connected to the external monitor data generation unit 36, and the operation image generation unit 37 is connected to the display control unit 33. In addition, a terminal-side connection terminal T2 and a display unit 34 are connected to the display control unit 33. Further, an operation unit 39 is disposed so as to be superimposed on the display unit 34.

Furthermore, a main body control unit 38 is connected to the display control unit 33, the communication control unit 35, the external monitor data generation unit 36, the operation image generation unit 37, and the operation unit 39. A storage unit 40 is connected to the main body control unit 38. Here, the terminal-side wireless communication unit 32 and the main body control unit 38 are connected such that information can be bidirectionally transmitted and received. The main body control unit 38 and the storage unit 40 are connected such that information can be bidirectionally transmitted and received.

Further, a terminal-side processor 41 is configured by the display control unit 33, the communication control unit 35, the external monitor data generation unit 36, the operation image generation unit 37, and the main body control unit 38.

The transducer array 11 of the ultrasound probe 2 has a plurality of ultrasound transducers which are arranged one-dimensionally or two-dimensionally. Each of the transducers transmits ultrasonic waves according to a driving signal supplied from the transmitting unit 12, receives waves reflected from a subject, and outputs an analog reception signal. Each transducer is configured using an element in which electrodes are formed at both ends of a piezoelectric body consisting of, for example, a piezoelectric ceramic typified by lead zirconate titanate (PZT), a polymeric piezoelectric element typified by polyvinylidene difluoride (PVDF), and a piezoelectric single crystal typified by lead magnesium niobate-lead titanate (PMN-PT).

The ultrasound transmission and reception control unit 15 controls the transmitting unit 12 and the receiving unit 13 of the transmitting and receiving unit 14 to perform the transmission of ultrasound beams and the reception of ultrasound echoes on the basis of an inspection mode and a scanning method instructed by the probe control unit 21. Here, it is assumed that the inspection mode indicates any one of the inspection modes that can be used in the ultrasound diagnostic apparatus, such as a brightness (B) mode, a motion (M) mode, a color Doppler (CD) mode, a power Doppler (PD) mode, a pulse Doppler (PW) mode, and a continuous wave Doppler (CW), and the scanning method indicates any one of an electronic sector scanning method, an electronic linear scanning method, or an electronic convex scanning method.

The transmitting unit 12 of the transmitting and receiving unit 14 includes, for example, a plurality of pulse generators, adjusts the amount of delay of each driving signal on the basis of a transmission delay pattern selected according to a control signal from the ultrasound transmission and reception control unit 15 such that the ultrasonic waves transmitted from the plurality of transducers of the transducer array 11 form an ultrasound beam, and supplies the driving signals to the plurality of transducers. As such, in a case in which a pulsed or continuous-wave voltage is applied to the electrodes of the transducers of the transducer array 11, the piezoelectric body is expanded and contracted and pulsed or continuous ultrasonic waves are generated from each transducer. An ultrasound beam whose focus has been narrowed down on a certain scanning line is formed from a combined wave of the ultrasonic waves.

The transmitted ultrasound beam is reflected by a target, such as a part of the subject, and is propagated as a so-called ultrasound echo toward the transducer array 11. The ultrasound echoes propagated toward the transducer array 11 in this way are received by each of the ultrasound transducers forming the transducer array 11. In this case, each of the ultrasound transducers forming the transducer array 11 receives the propagated ultrasound echoes, is expanded and contracted to generate an electric signal, and outputs the electric signal to the receiving unit 13.

Figure 2:
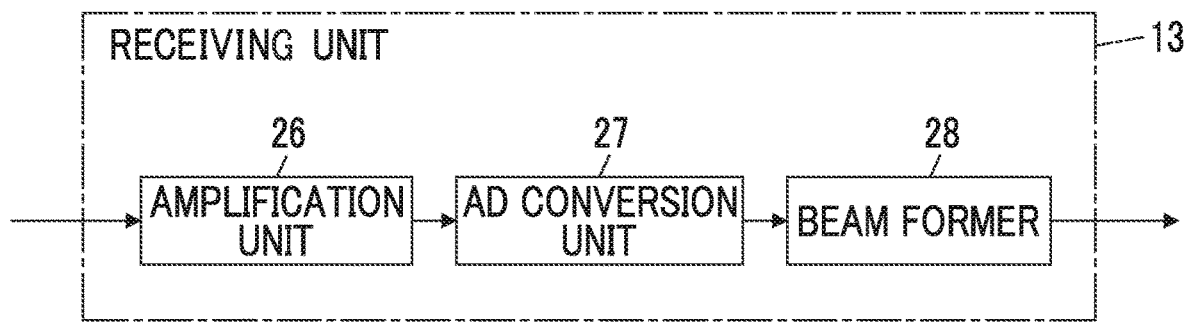
FIG. 2 is a block diagram illustrating an internal configuration of a receiving unit in Embodiment 1 of the invention.

The receiving unit 13 of the transmitting and receiving unit 14 processes the reception signal output from the transducer array 11 according to a control signal from the ultrasound transmission and reception control unit 15. As illustrated in FIG. 2, the receiving unit 13 has a configuration in which an amplification unit 26, an analog digital (AD) conversion unit 27, and a beam former 28 are connected in series to each other. The amplification unit 26 amplifies the reception signal which is an analog signal input from each of the ultrasound transducers forming the transducer array 11 and transmits the amplified reception signal to the AD conversion unit 27. The AD conversion unit 27 converts the analog reception signal transmitted from the amplification unit 26 into a digital signal to acquire reception data, and transmits the reception data to the beam former 28. The beam former 28 performs a reception focusing process which gives a delay to each reception data item following the set sound velocity on the basis of a reception delay pattern selected according to a control signal from the ultrasound transmission and reception control unit 15 and performs addition (phasing addition). The sound ray signal in which the focus of the ultrasound echo is narrowed down on a certain scanning line is generated by the reception focusing process.

The image information data generation unit 19 of the probe-side processor 25 generates image information data on the basis of the sound ray signal generated by the beam former 28 of the receiving unit 13.

Here, the signal processing unit 16 of the image information data generation unit 19 corrects the attenuation of the sound ray signal generated by the beam former 28 of the receiving unit 13 caused by a propagation distance according to the depth of the position where the ultrasonic waves are reflected and performs an envelope detection process on the sound ray signal to generate a signal indicating tomographic image information related to the tissues in the subject.

The image processing unit 17 of the image information data generation unit 19 raster-converts the signal generated by the signal processing unit 16 into an image signal following a general television signal scanning method, performs various types of necessary image processing, such as brightness correction, gradation correction, sharpness correction, image size correction, refresh rate correction, scanning frequency correction, and color correction following a display format for the display unit 34 of the mobile information terminal 3, on the generated image signal to generate an ultrasound image signal, and transmits the ultrasound image signal as image information data to the probe-side wireless communication unit 18 or the probe-side connection terminal T1.

The probe-side wireless communication unit 18 of the ultrasound probe 2 includes an antenna for transmitting and receiving radio waves and modulates a carrier on the basis of the ultrasound image signal generated by the image information data generation unit 19 to generate a transmission signal indicating the ultrasound image signal. The probe-side wireless communication unit 18 supplies the generated transmission signal indicating the ultrasound image signal to the antenna and transmits radio waves from the antenna to wirelessly transmit the ultrasound image signal in sequence. For example, amplitude shift keying (ASK), phase shift keying (PSK), quadrature phase shift keying (QPSK), and 16 quadrature amplitude modulation (16QAM) can be used as the carrier modulation method.

In addition, the probe-side wireless communication unit 18 receives a transmission signal indicating probe operation information for operating the ultrasound probe 2 from the mobile information terminal 3 and transmits the probe operation information acquired by demodulating the received transmission signal to the probe control unit 21. For example, the probe operation information is input by the user through the operation unit 39 of the mobile information terminal 3, which will be described below.

The communication control unit 20 of the probe-side processor 25 controls the probe-side wireless communication unit 18 such that the ultrasound image signal is transmitted with transmission radio field intensity set by the probe control unit 21. Further, the communication control unit 20 of the probe-side processor 25 controls the probe-side wireless communication unit 18 such that the probe operation information wirelessly transmitted from the mobile information terminal 3 is received.

The probe-side connection terminal T1 of the ultrasound probe 2 is a terminal that is used in a case in which the ultrasound probe 2 and the mobile information terminal 3 are connected in a wired manner and information is bidirectionally transmitted and received between the ultrasound probe 2 and the mobile information terminal 3. In this case, for example, a connection cable capable of transmitting information is inserted into the probe-side connection terminal T1.

The probe control unit 21 of the probe-side processor 25 controls each unit of the ultrasound probe 2 on the basis of, for example, a program stored in advance.

The battery 22 of the ultrasound probe 2 is provided in the ultrasound probe 2 and supplies power to each circuit of the ultrasound probe 2.

The terminal-side wireless communication unit 32 of the mobile information terminal 3 includes an antenna for transmitting and receiving radio waves, receives the transmission signal indicating the ultrasound image signal transmitted by the probe-side wireless communication unit 18 of the ultrasound probe 2 through the antenna, and transmits the ultrasound image signal output by demodulating the received transmission signal to the display control unit 33. Further, the terminal-side wireless communication unit 32 modulates the carrier on the basis of the probe operation information for operating the ultrasound probe 2 which has been transmitted from the main body control unit 38 to generate a transmission signal indicating the probe operation information, and wirelessly transmits the generated transmission signal to the probe-side wireless communication unit 18 of the ultrasound probe 2.

Further, the terminal-side wireless communication unit 32 modulates the carrier on the basis of the external monitor data generated by the external monitor data generation unit 36 to generate a transmission signal indicating the external monitor data and wirelessly transmits the generated transmission signal to the external monitor 4, which will be described below. The external monitor data includes an external monitor ultrasound image signal having the display format of the external monitor 4, which will be described below. For example, ASK, PSK, QPSK, and 16QAM are used as the carrier modulation method in the terminal-side wireless communication unit 32, similarly to the carrier modulation method in the probe-side wireless communication unit 18.

The communication control unit 35 of the terminal-side processor 41 controls the terminal-side wireless communication unit 32 of the mobile information terminal 3 such that the transmission signal indicating the ultrasound image signal is received from the probe-side wireless communication unit 18 of the ultrasound probe 2. In addition, the communication control unit 35 of the terminal-side processor 41 controls the terminal-side wireless communication unit 32 such that data is wirelessly transmitted to each of the ultrasound probe 2 and the external monitor 4 with transmission radio field intensity set by the main body control unit 38.

The operation unit 39 of the mobile information terminal 3 is used by the user to perform an input operation and includes a touch sensor that is disposed so as to be superimposed on the display unit 34. For example, the user inputs the probe operation information for operating the ultrasound probe 2 through the operation unit 39. The input probe operation information is wirelessly transmitted from the terminal-side wireless communication unit 32 to the ultrasound probe 2 through the main body control unit 38 of the terminal-side processor 41. In addition, for example, the user inputs external monitor operation information for operating the external monitor 4 through the operation unit 39. The input external monitor operation information is wirelessly transmitted from the terminal-side wireless communication unit 32 to the external monitor 4 through the main body control unit 38 of the terminal-side processor 41.

Figure 3:
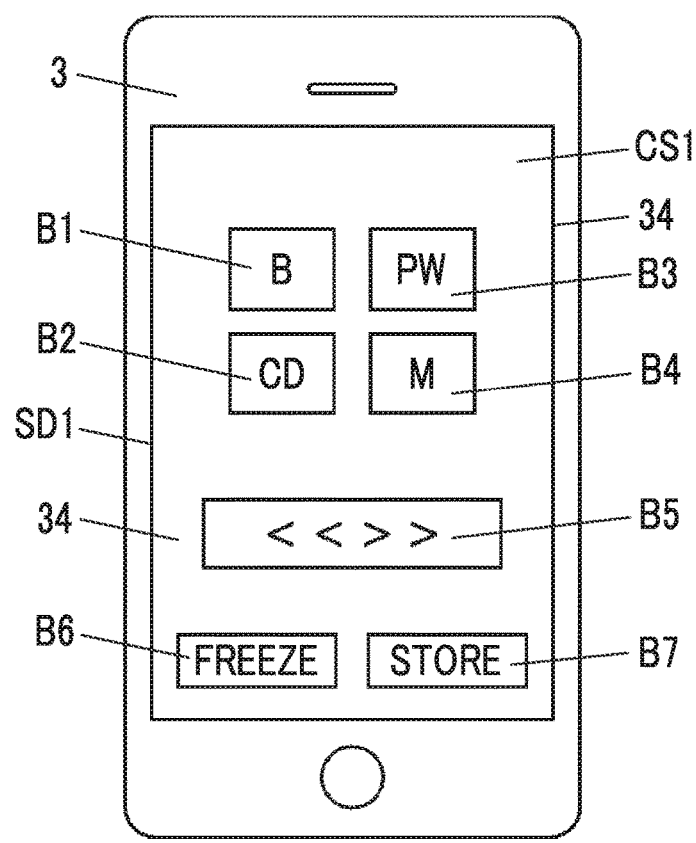
FIG. 3 is a diagram schematically illustrating an operation image displayed on a mobile information terminal in Embodiment 1 of the invention.

The operation image generation unit 37 of the terminal-side processor 41 generates an operation image which is displayed on the display unit 34 of the mobile information terminal 3 and is used by the user to perform an input operation through the touch sensor of the operation unit 39. For example, as illustrated in FIG. 3, an operation image CS1 includes various operation buttons including a B-mode button B1 for determining the inspection mode of the ultrasound probe 2 as the B-mode. The user touches the operation buttons to input, for example, the probe operation information and the external monitor operation information through the touch sensor of the operation unit 39.

In the example illustrated in FIG. 3, a terminal-side display screen SD1 of the display unit 34 of the mobile information terminal 3 has a second size that is smaller than a first size of an external-monitor-side display screen of the external monitor 4 which will be described below. The operation image CS1 has a size equal to the second size of the terminal-side display screen SD1 and includes a CD-mode button B2 for determining the inspection mode as the CD-mode, a PW-mode button B3 for determining the inspection mode as the PW-mode, an M-mode button B4 for determining the inspection mode as the M-mode, a scroll button B5 for scroll display, a freeze button B6 for the freeze display of the ultrasound image, and a storage button B7 for storing the ultrasound image in addition to the B-mode button B1.

The external monitor data generation unit 36 of the terminal-side processor 41 generates data corresponding to the external monitor ultrasound image that can be displayed on the external monitor 4 and the operation image CS1 as external monitor data having a display format for the external monitor 4, on the basis of the ultrasound image signal output from the terminal-side wireless communication unit 32 and the operation image CS1 generated by the operation image generation unit 37. In this case, the external monitor data generation unit 36 performs various types of necessary image processing, such as brightness correction, gradation correction, sharpness correction, image size correction, refresh rate correction, scanning frequency correction, and color correction following the display format for the external monitor 4, on the ultrasound image signal output from the terminal-side wireless communication unit 32 to generate an ultrasound image signal for the external monitor 4 as the data corresponding to the external monitor ultrasound image.

Under the control of the main body control unit 38, the display control unit 33 of the terminal-side processor 41 performs predetermined processing on the ultrasound image signal output from the terminal-side wireless communication unit 32 and the operation image CS1 generated by the operation image generation unit 37 and displays, on the display unit 34, the operation image CS1 and a terminal ultrasound image that has the display format for the display unit 34 of the mobile information terminal 3 and can be displayed on the display unit 34.

The display unit 34 of the mobile information terminal 3 displays the terminal ultrasound image and the operation image CS1 under the control of the display control unit 33. For example, the display unit 34 includes a display device such as a liquid crystal display (LCD) or an organic electroluminescence (EL) display.

The terminal-side connection terminal T2 of the mobile information terminal 3 is a terminal that is used in a case in which the ultrasound probe 2 and the mobile information terminal 3 are connected in a wired manner and information is bidirectionally transmitted and received between the ultrasound probe 2 and the mobile information terminal 3, similarly to the probe-side connection terminal T1 of the ultrasound probe 2. For example, the terminal-side connection terminal T2 is connected to the other end of a connection cable that has one end connected to the probe-side connection terminal T1 and is capable of transmitting information.

The storage unit 40 of the mobile information terminal 3 stores, for example, an operation program for the mobile information terminal 3. For example, a random access memory (RAM), a secure digital card (SD card), or a solid state drive (SSD) can be used as the storage unit 40.

Here, the probe-side processor 25 including the transmitting unit 12, the receiving unit 13, the ultrasound transmission and reception control unit 15, the signal processing unit 16, the image processing unit 17, the communication control unit 20, and the probe control unit 21 in the ultrasound probe 2 and the terminal-side processor 41 including the display control unit 33, the communication control unit 35, the external monitor data generation unit 36, the operation image generation unit 37, and the main body control unit 38 in the mobile information terminal 3 are implemented by a central processing unit (CPU) and a control program for causing the CPU to perform various processes. However, the processors may be implemented by a field programmable gate array (FPGA), a digital signal processor (DSP), an application specific integrated circuit (ASIC), a graphics processing unit (GPU), other integrated circuits (ICs), or combinations thereof.

Some or all of the transmitting unit 12, the receiving unit 13, the ultrasound transmission and reception control unit 15, the signal processing unit 16, the image processing unit 17, the communication control unit 20, and the probe control unit 21 of the probe-side processor 25 may be integrated into, for example, one CPU. Similarly, some or all of the display control unit 33, the communication control unit 35, the external monitor data generation unit 36, the operation image generation unit 37, and the main body control unit 38 of the terminal-side processor 41 may be integrated into, for example, one CPU.

Figure 4:
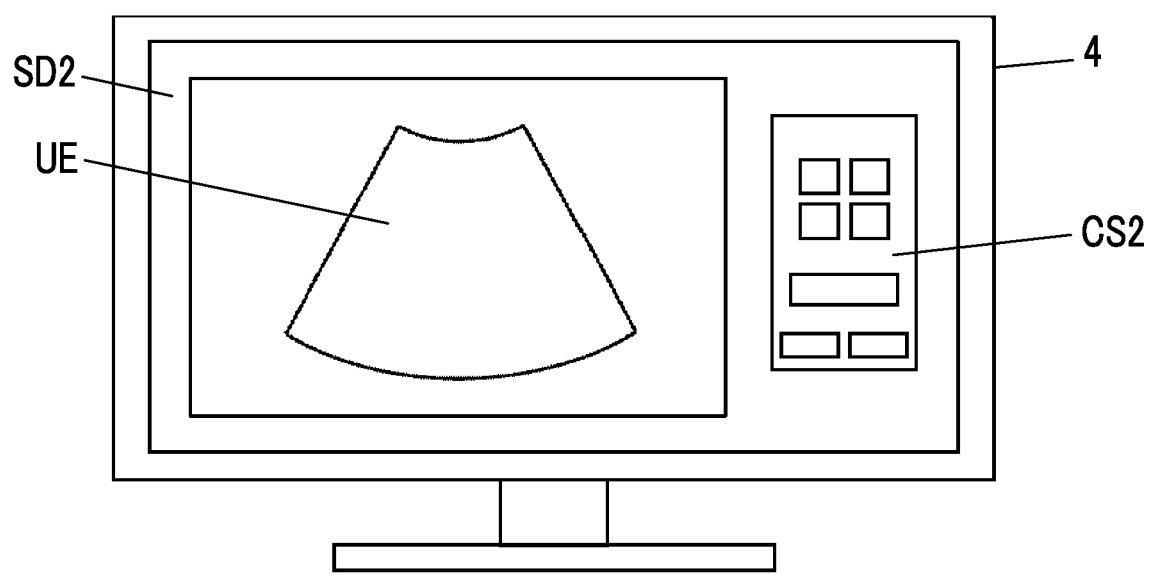
FIG. 4 is a diagram schematically illustrating an image displayed on an external monitor in Embodiment 1 of the invention.

As illustrated in FIG. 4, the external monitor 4 of the ultrasound system 1 has an external-monitor-side display screen SD2 having the first size that is larger than the second size of the terminal-side display screen SD1 of the mobile information terminal 3 and displays an external monitor ultrasound image UE and an external monitor operation image CS2 that follow the display format of the external monitor 4 on the basis of the external monitor data wirelessly transmitted from the mobile information terminal 3. In this case, the external monitor 4 displays, as the external monitor operation image CS2, the same operation image as the operation image CS1 that is currently displayed on the display unit 34 of the mobile information terminal 3.

Next, the operation of the ultrasound system 1 according to Embodiment 1 of the invention will be described.

First, in the mobile information terminal 3, the operation image generation unit 37 of the terminal-side processor 41 generates the operation image CS1 that is displayed on the display unit 34 and is used by the user to perform an input operation through the touch sensor of the operation unit 39. As illustrated in FIG. 3, the operation image CS1 can include, for example, buttons for operating the ultrasound probe 2, such as the B-mode button B1 and the CD-mode button B2, and buttons for operating the external monitor 4 such as the scroll button B5. The generated operation image CS1 is displayed on the display unit 34 of the mobile information terminal 3 under the control of the display control unit 33, as illustrated in FIG. 3.

Then, the user inputs an inspection mode used for diagnosis as the probe operation information through the touch sensor of the operation unit 39 according to the operation image CS1 displayed on the display unit 34 of the mobile information terminal 3. In this case, for example, the user touches the B-mode button B1 of the operation image CS1 illustrated in FIG. 3 to input the probe operation information indicating that the B-mode is used as the inspection mode. Hereinafter, for the sake of description, it is assumed that the B-mode is used as the inspection mode.

In a case in which the user inputs the probe operation information indicating that the B-mode is used as the inspection mode in this way, the probe operation information input by the user is transmitted to the terminal-side wireless communication unit 32 of the mobile information terminal 3 through the main body control unit 38 of the terminal-side processor 41 and is then wirelessly transmitted from the terminal-side wireless communication unit 32 to the ultrasound probe 2. The probe operation information wirelessly transmitted from the terminal-side wireless communication unit 32 is received by the probe-side wireless communication unit 18, is transmitted to the probe control unit 21, and is then transmitted from the probe control unit 21 to each of the ultrasound transmission and reception control unit 15, the signal processing unit 16, and the image processing unit 17. In this way, the inspection mode used for diagnosis is set to the B-mode.

The ultrasound transmission and reception control unit 15 of the probe-side processor 25 controls the transmitting and receiving unit 14 such that ultrasonic waves are transmitted and received in the transducer array 11, on the basis of the probe operation information indicating that the B-mode is used as the inspection mode which has been transmitted from the probe control unit 21. In this case, first, ultrasound beams are transmitted into the subject from the plurality of ultrasound transducers of the transducer array 11 according to the driving signal from the transmitting unit 12 of the transmitting and receiving unit 14 under the control of the ultrasound transmission and reception control unit 15. Ultrasound echoes from the subject, which are based on the transmitted ultrasound beams, are received by each ultrasound transducer and a reception signal which is an analog signal is output to the receiving unit 13, is amplified by the amplification unit 26, and is converted into a digital signal by the AD conversion unit 27. As a result, reception data is acquired. The beam former 28 performs a reception focusing process on the reception data to generate a sound ray signal.

The signal processing unit 16 of the image information data generation unit 19 performs predetermined signal processing on the sound ray signal generated by the beam former 28 of the receiving unit 13 to generate a signal indicating a tomographic image of the tissues in the subject. In this case, the signal processing unit 16 generates the signal indicating the tomographic image on the basis of the information indicating the inspection mode transmitted by the probe control unit 21, that is, the probe operation information indicating that the B-mode is used as the inspection mode.

The image processing unit 17 raster-converts the signal generated by the signal processing unit 16 into an image signal following the general television signal scanning method. Then, various types of necessary image processing, such as brightness correction, gradation correction, sharpness correction, image size correction, refresh rate correction, scanning frequency correction, and color correction following the display format for the display unit 34 of the mobile information terminal 3, are performed on the image signal to generate an ultrasound image signal as the image information data.

The ultrasound image signal generated by the image processing unit 17 is wirelessly transmitted to the terminal-side wireless communication unit 32 of the mobile information terminal 3 through the probe-side wireless communication unit 18 and is then transmitted from the terminal-side wireless communication unit 32 to the display control unit 33 and the external monitor data generation unit 36.

The ultrasound image signal transmitted from the terminal-side wireless communication unit 32 to the display control unit 33 is displayed as the terminal ultrasound image following the display format for the mobile information terminal 3 on the display unit 34 of the mobile information terminal 3 under the control of the display control unit 33. In this case, the display of the operation image CS1 on the display unit 34 is switched to the display of the terminal ultrasound image, which is not illustrated.

Here, in a state in which the terminal ultrasound image is displayed on the display unit 34 of the mobile information terminal 3, the user can input information indicating that an ultrasound image is to be displayed on the external monitor 4 through the touch sensor of the operation unit 39. For example, an external monitor display button for inputting information indicating that an ultrasound image is displayed on the external monitor 4 is displayed on the display unit 34, which is not illustrated. The user touches the external monitor display button through the touch sensor of the operation unit 39 to input monitor operation information indicating that an ultrasound image is displayed on the external monitor 4. The input information is transmitted to the main body control unit 38 and is then transmitted from the main body control unit 38 to the external monitor data generation unit 36. In this case, the display of the terminal ultrasound image on the display unit 34 is switched to the display of the operation image CS1.

In a case in which the external monitor data generation unit 36 receives the information indicating that the ultrasound image is displayed on the external monitor 4 from the main body control unit 38, it performs various types of necessary image processing, such as brightness correction, gradation correction, sharpness correction, image size correction, refresh rate correction, scanning frequency correction, and color correction following the display format for the external monitor 4, on the basis of the ultrasound image signal transmitted from the terminal-side wireless communication unit 32 to the external monitor data generation unit 36 to generate an ultrasound image signal for the external monitor 4. In addition, the external monitor data generation unit 36 performs various types of necessary image processing, such as brightness correction, gradation correction, sharpness correction, image size correction, refresh rate correction, scanning frequency correction, and color correction following the display format for the external monitor 4, on the operation image generated by the operation image generation unit 37 to generate data corresponding to the operation image for the external monitor 4.

The external monitor data generation unit 36 generates external monitor data including the generated ultrasound image signal for the external monitor 4 and the data corresponding to the operation image for the external monitor 4 and transmits the external monitor data to the terminal-side wireless communication unit 32 of the mobile information terminal 3. The external monitor data transmitted from the external monitor data generation unit 36 to the terminal-side wireless communication unit 32 is wirelessly transmitted from the terminal-side wireless communication unit 32 to the external monitor 4.

The external monitor 4 displays the external monitor ultrasound image UE and the external monitor operation image CS2 that is the same as the operation image CS1 currently displayed on the display unit 34 of the mobile information terminal 3 in the external-monitor-side display screen SD2 having the first size, on the basis of the external monitor data wirelessly transmitted from the mobile information terminal 3, as illustrated in FIG. 4. As illustrated in FIG. 4, the external monitor operation image CS2 having the second size smaller than the first size and the external monitor ultrasound image UE having a third size that is smaller than the first size and is larger than the second size are displayed on the external-monitor-side display screen S2 of the external monitor 4.

In a case in which the user performs an input operation through the touch sensor of the operation unit 39 according to the operation image CS1 displayed on the display unit 34 of the mobile information terminal 3 with the external monitor ultrasound image UE and the external monitor operation image CS2 displayed on the external monitor 4, an operation related to display on the external monitor 4 is performed. For example, as illustrated in FIG. 3, the user touches the freeze button B6 displayed on the display unit 34 of the mobile information terminal 3 to freeze the display of the external monitor ultrasound image UE on the external monitor 4.

In this way, the operation of the ultrasound system 1 according to the invention is performed.

However, in a so-called stationary ultrasound diagnostic apparatus according to the related art, in many cases, an operation console for performing an input operation on the ultrasound diagnostic apparatus and a display monitor for displaying an ultrasound image are integrally configured. In a case in which the stationary ultrasound diagnostic apparatus is used, the user may diagnose the subject at a position away from the operation console and the display monitor of the ultrasound diagnostic apparatus. In this case, it is difficult for the user to directly touch the operation console to perform the operation of the ultrasound diagnostic apparatus required for diagnosis. In addition, it is difficult for the user to check the ultrasound image displayed on the display monitor. According to the ultrasound system 1 of the invention, the mobile information terminal 3 has the operation unit 39. Therefore, for example, the user can easily perform an input operation related to the operation of the ultrasound probe 2 and the external monitor 4 by operating the mobile information terminal 3 with one hand while handling the ultrasound probe 2 with the other hand. Further, in the invention, the external monitor ultrasound image UE can be displayed on the external monitor 4. Therefore, for example, the user can dispose the external monitor 4 in the vicinity of the subject to more clearly check the ultrasound image.

Further, the external monitor operation image CS2 that is the same as the operation image CS1 currently displayed on the display unit 34 of the mobile information terminal 3 is displayed on the external monitor 4. Therefore, in a case in which the user performs an input operation through the touch sensor of the operation unit 39, the user can perform the input operation while checking the external monitor operation image CS2 displayed on the external monitor 4, instead of checking the operation image CS1 displayed on the display unit 34 of the mobile information terminal 3.

Furthermore, according to the ultrasound system 1 of the invention, the external monitor data generation unit 36 of the mobile information terminal 3 generates the ultrasound image signal following the display format for the external monitor 4 and the data corresponding to the external monitor operation image CS2. Therefore, a general-purpose monitor device can be used as the external monitor 4. Therefore, the user can select the monitor device used as the external monitor 4 according to the purpose and configure the ultrasound system 1 according to the purpose.

As described above, according to the ultrasound system 1 of the invention, it is possible to improve convenience in ultrasound diagnosis while enabling the user to easily perform the observation of the ultrasound image and an input operation for ultrasound diagnosis.

Furthermore, in Embodiment 1, the external monitor operation image CS2 is displayed on the external monitor 4. However, only the external monitor ultrasound image UE may be displayed on the external monitor 4 and the external monitor operation image CS2 may not be displayed. As such, even in a case in which only the external monitor ultrasound image UE is displayed on the external monitor 4, it is possible to improve convenience in ultrasound diagnosis while enabling the user to easily perform the observation of the ultrasound image and an input operation for ultrasound diagnosis. However, the display of the external monitor operation image CS2 on the external monitor 4 makes it possible to further improve convenience in ultrasound diagnosis.

Further, in Embodiment 1, the B-mode is used as the inspection mode. However, for example, the M-mode may be used. Furthermore, the image information data generation unit 19 may comprise a Doppler processing unit that performs so-called Doppler processing such that the CD-mode, the PD-mode, the PW-mode, the CW-mode, and the like are used, which is not illustrated.

Further, in this case, it is desirable that a button for inputting probe operation information indicating that the M-mode, the CD-mode, the PD-mode, the PW-mode, the CW-mode, or the like is used as the inspection mode is included in the operation image CS1 as a button for setting the inspection mode.

In addition, for example, a measurement menu for selecting measurement items in a case in which measurement is performed on the ultrasound image, a user interface, such as a keyboard for inputting information of the subject, and a menu for selecting a body mark displayed so as to be superimposed on the ultrasound image may be displayed on the operation image CS1, which is not illustrated. Here, the measurement items include, for example, the measurement of the distance between two points on the ultrasound image, the measurement of the area of a part on the ultrasound image, and the measurement of a blood flow rate using Doppler signals.

Further, in a case in which the distance, the area, and the like are measured on the ultrasound image, for example, a measurement unit for performing processes related to the measurement may be provided in the mobile information terminal 3, which is not illustrated. In this case, the user can touch, for example, a measurement caliper on the terminal ultrasound image displayed on the display unit 34 of the mobile information terminal 3 to measure the distance, the area, and the like on the ultrasound image. In this case, the external monitor data generation unit 36 can generate, as the external monitor data, data which corresponds to the same display as that currently performed on the display unit 34 of the mobile information terminal 3 and follows the display format for the external monitor 4 and transmit the data to the external monitor 4 through the terminal-side wireless communication unit 32. Therefore, the user can perform measurement on the ultrasound image while checking display on the external monitor 4, instead of checking display on the display unit 34 of the mobile information terminal 3.

In addition, a body mark that is displayed so as to be superimposed on the ultrasound image may be displayed on the display unit 34 of the mobile information terminal 3 and a probe mark that is further displayed so as to be superimposed on the displayed body mark may be displayed. The position of the displayed probe mark may be adjusted by a touch operation. In this case, the external monitor data generation unit 36 can generate, as the external monitor data, data which corresponds to the same display as that currently performed on the display unit 34 of the mobile information terminal 3 and follows the display format for the external monitor 4 and transmit the data to the external monitor 4 through the terminal-side wireless communication unit 32. Therefore, the user can adjust the position of the probe mark while checking display on the external monitor 4, instead of checking display on the display unit 34 of the mobile information terminal 3.

In addition, a small ultrasound image which corresponds to the ultrasound image signal sequentially transmitted from the terminal-side wireless communication unit 32 and is used to check the operation of the ultrasound system 1 may be displayed on the operation image CS1 displayed on the display unit 34 of the mobile information terminal 3. In this case, the user can see the display unit 34 of the mobile information terminal 3, instead of the external monitor 4, to check that the ultrasound probe 2 is currently operating and ultrasound image signals are sequentially acquired.

Further, in a case in which the user touches various buttons included in the operation image CS1 displayed on the display unit 34 of the mobile information terminal 3, the display aspect of the button touched by the user may be changed. For example, the color of the button touched by the user may be changed, or the color of the contour of the button touched by the user may be changed. Therefore, even in the external monitor operation image CS2 displayed on the external monitor 4, the display aspect of the same button as that touched by the user in the operation image CS1 displayed on the display unit 34 of the mobile information terminal 3 is changed. In this case, the user can check the external monitor operation image CS2 displayed on the external monitor 4 to more clearly understand what input operation is currently performed by the user.

In addition, the mobile information terminal 3 may comprise a voice recognition unit that recognizes the voice of the user, which is not illustrated. In this case, input operations, such as the setting of the inspection mode and the freeze display of the external monitor ultrasound image UE on the external monitor 4, can be performed by the voice of the user.

Further, a mechanical operation button that is provided in advance in the mobile information terminal 3 may be used to perform an input operation in the ultrasound system 1.

As such, a plurality of input methods can be provided for the input operation of the user to further improve convenience in ultrasound diagnosis.

Furthermore, in Embodiment 1, wireless communication is performed between the ultrasound probe 2 and the mobile information terminal 3 and between the mobile information terminal 3 and the external monitor 4. However, it is desirable that a wireless communication method between the ultrasound probe 2 and the mobile information terminal 3 and a wireless communication method between the mobile information terminal 3 and the external monitor 4 are different from each other in order to keep each wireless communication state good.

For example, a frequency band in the wireless communication between the ultrasound probe 2 and the mobile information terminal 3 can be different from a frequency band in the wireless communication between the mobile information terminal 3 and the external monitor 4. For example, specifically, a frequency in a band of 2.4 GHz can be used for the wireless communication between the ultrasound probe 2 and the mobile information terminal 3, and a frequency in a band of 5 GHz can be used for the wireless communication between the mobile information terminal 3 and the external monitor 4. Further, for example, a communication standard used for the wireless communication between the ultrasound probe 2 and the mobile information terminal 3 may be different from a communication standard used for the wireless communication between the mobile information terminal 3 and the external monitor 4.

Figure 5:
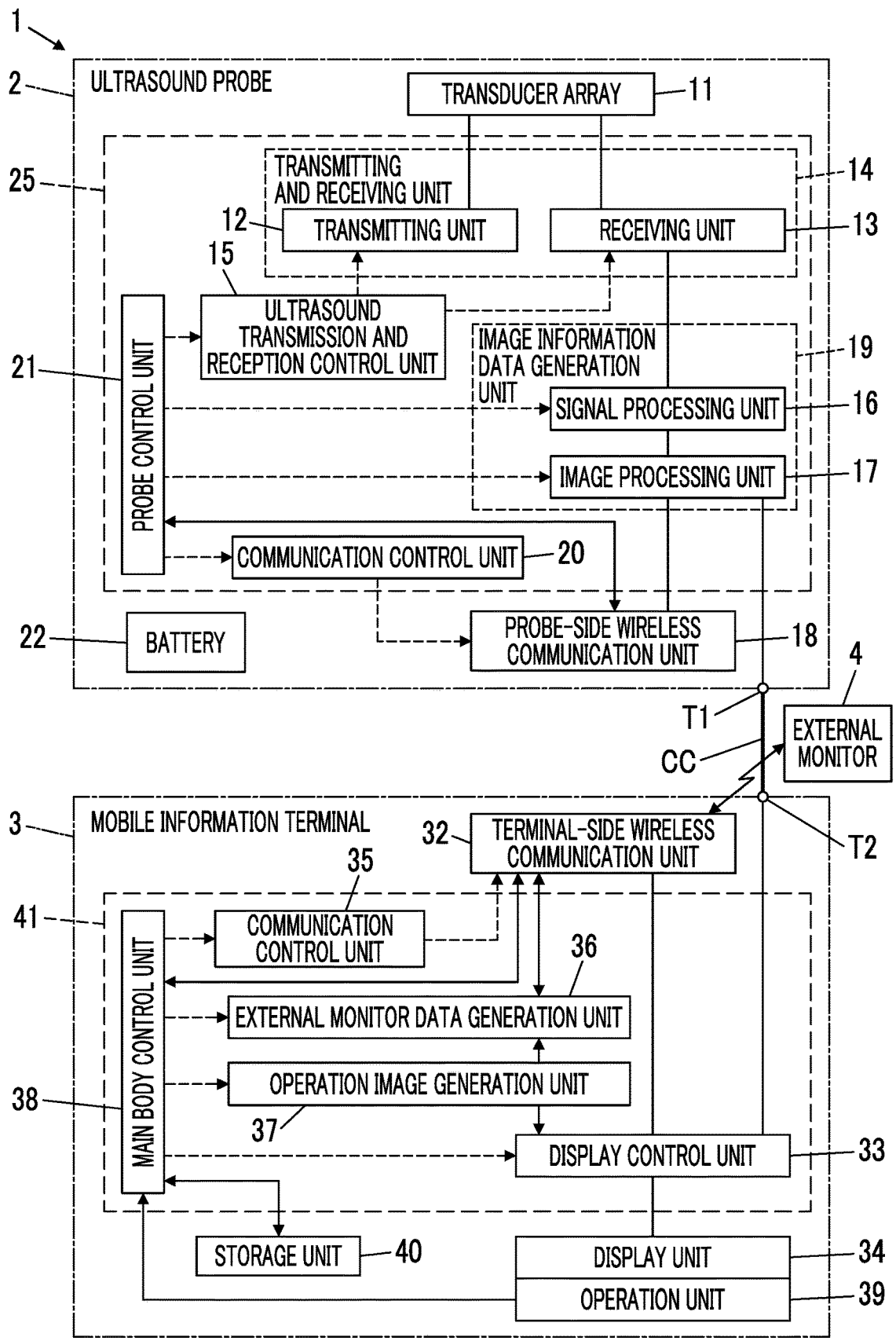
FIG. 5 is a block diagram illustrating a configuration of an ultrasound system according to a modification example of Embodiment 1 of the invention.

Further, the ultrasound probe 2 and the mobile information terminal 3 may not be wirelessly connected, but may be connected in a wired manner. Specifically, as illustrated in FIG. 5, the ultrasound probe 2 and the mobile information terminal 3 can be connected in a wired manner by connecting the probe-side connection terminal T1 of the ultrasound probe 2 and the terminal-side connection terminal T2 of the mobile information terminal 3 using a connection cable CC capable of transmitting information. In this case, in the ultrasound system 1, the connection of the connection cable CC to the probe-side connection terminal T1 and the terminal-side connection terminal T2 can be detected to stop the wireless connection between the ultrasound probe 2 and the mobile information terminal 3.

In this way, it is possible to stabilize the communication state between the ultrasound probe 2 and the mobile information terminal 3.

Further, in Embodiment 1, the terminal ultrasound image is displayed on the display unit 34 of the mobile information terminal 3. However, the external monitor ultrasound image UE may be always displayed on the external monitor 4, instead of displaying only the operation image CS1 on the display unit 34 of the mobile information terminal 3.

In a case in which the external monitor ultrasound image UE is not displayed on the external monitor 4, the operation image CS1 and the terminal ultrasound image can be displayed on the display unit 34 of the mobile information terminal 3. For example, the mobile information terminal 3 may be provided with a connection detection unit that detects whether or not the mobile information terminal 3 and the external monitor 4 are connected to each other, which is not illustrated. In a case in which the connection detection unit determines that the mobile information terminal 3 and the external monitor 4 are not connected to each other, the operation image CS1 and the terminal ultrasound image can be displayed on the mobile information terminal 3. In a case in which the connection detection unit determines that the mobile information terminal 3 and the external monitor 4 are connected to each other, it is possible to display the external monitor ultrasound image UE on the external monitor 4, instead of displaying only the operation image CS1 on the mobile information terminal 3.

Here, for example, the connection detection unit can wirelessly transmit a connection check signal for checking whether or not the mobile information terminal 3 and the external monitor 4 are connected to each other to the external monitor 4 through the terminal-side wireless communication unit 32 to determine whether or not the mobile information terminal 3 and the external monitor 4 are connected to each other. In this case, for example, a reception confirmation signal indicating that the connection check signal wirelessly transmitted from the mobile information terminal 3 has been received is wirelessly transmitted from the external monitor 4 to the mobile information terminal 3. The connection detection unit receives the wirelessly transmitted reception confirmation signal through the terminal-side wireless communication unit 32. Therefore, the connection detection unit can determine that the mobile information terminal 3 and the external monitor 4 are wirelessly connected to each other. Further, for example, the connection detection unit can determine that the mobile information terminal 3 and the external monitor 4 are not connected to each other in a case in which it does not receive any signal from the external monitor 4 due to the turn-off of the external monitor 4, the deterioration of the wireless communication state between the mobile information terminal 3 and the external monitor 4, or the like and in a case in which a signal indicating an error is received from the external monitor 4, as a result of wirelessly transmitting the connection check signal to the external monitor 4. Furthermore, even in a case in which the mobile information terminal 3 and the external monitor 4 do not perform wireless communication, but perform wired communication, the connection detection unit can determine whether or not the mobile information terminal 3 and the external monitor 4 are connected to each other, using the same method.

Further, for example, in a case in which the operation image CS1 and the terminal ultrasound image are displayed in the mobile information terminal 3, the operation image CS1 and the terminal ultrasound image may be displayed on the display unit 34 of the mobile information terminal 3 at the same time or may be displayed while being switched. In this case, the user can perform an ultrasound diagnosis on the subject while checking the display unit 34 of the mobile information terminal 3 even in a case in which the external monitor ultrasound image UE is not displayed on the external monitor 4.

Further, an external data memory that stores, for example, the ultrasound image signal transmitted from the terminal-side wireless communication unit 32 may be connected to the mobile information terminal 3, which is not illustrated. The following can be used as the external data memory: a recording medium, such as a hard disc drive (HDD), an SSD, a flexible disc (FD), a magneto-optical disc (MO disc), a magnetic tape (MT), a RAM, a compact disc (CD), a digital versatile disc (DVD), a SD card, or a USB memory; or a sever. Further, the mobile information terminal 3 and the external data memory can be connected to each other wirelessly or in a wired manner.

Embodiment 2

Figure 6:
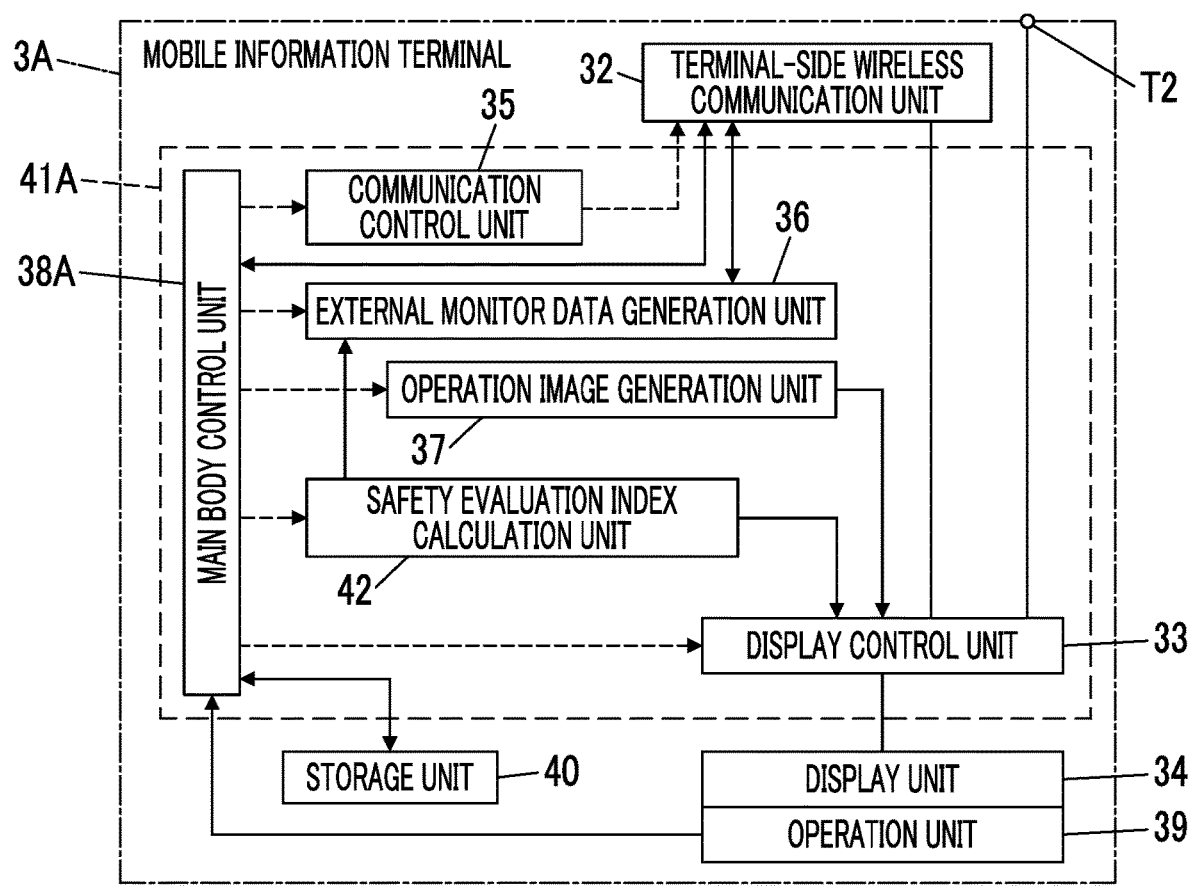
FIG. 6 is a block diagram illustrating a configuration of a mobile information terminal in Embodiment 2 of the invention.

An ultrasound system according to Embodiment 2 is different from the ultrasound system 1 according to Embodiment 1 illustrated in FIG. 1 in that it comprises a mobile information terminal 3A illustrated in FIG. 6, instead of the mobile information terminal 3. The mobile information terminal 3A according to Embodiment 2 is different from the mobile information terminal 3 illustrated in FIG. 1 in that a main body control unit 38A is provided instead of the main body control unit 38 and a safety evaluation index calculation unit 42 is added.

In the mobile information terminal 3A, the safety evaluation index calculation unit 42 is connected to the display control unit 33 and the safety evaluation index calculation unit 42 is connected to the external monitor data generation unit 36. Further, the main body control unit 38A is connected to the display control unit 33, the communication control unit 35, the external monitor data generation unit 36, the operation image generation unit 37, and the safety evaluation index calculation unit 42.

Furthermore, a terminal-side processor 41A is configured by the display control unit 33, the communication control unit 35, the external monitor data generation unit 36, the operation image generation unit 37, the main body control unit 38A, and the safety evaluation index calculation unit 42.

The safety evaluation index calculation unit 42 of the terminal-side processor 41A calculates a safety evaluation index on the basis of ultrasound transmission and reception conditions controlled by the ultrasound transmission and reception control unit 15 of the ultrasound probe 2 illustrated in FIG. 1 and transmits the calculated safety evaluation index to the display control unit 33 and the external monitor data generation unit 36. Here, the ultrasound transmission and reception conditions controlled by the ultrasound transmission and reception control unit 15 of the probe-side processor 25 include, for example, the scanning rate of the transmitting and receiving unit 14 of the probe-side processor 25, the intensity of the ultrasonic waves transmitted from the transducer array 11 into the subject, that is, the level of the voltage of the driving signal transmitted by the transmitting unit 12, the center frequency of the ultrasonic waves, and the amplification factor of the reception signal.

Further, the safety evaluation index is an index for evaluating safety against the influence of ultrasonic waves on a living body and includes, for example, a mechanical index (MI) value for evaluating the safety of a mechanical action, such as the radiation pressure and vibration of the ultrasonic waves in the living body, and a thermal index (TI) value for evaluating safety against a living body heating action caused by the absorption of the energy of the ultrasonic waves in the living body.

For example, in a case in which the MI value is calculated as the safety evaluation index, the safety evaluation index calculation unit 42 can divide the maximum negative sound pressure of the ultrasonic waves considering attenuation in the living body by the square root of the center frequency of the ultrasonic waves transmitted from the transducer array 11 to calculate the MI value. In addition, in a case in which the TI value is calculated as the safety evaluation index, the safety evaluation index calculation unit 42 can divide the output intensity of the ultrasonic waves in the living body by the output intensity of the ultrasonic waves required to increase the temperature of the living tissues by 1° C. to calculate the TI value.

The safety evaluation indices, such as the MI value and the TI value calculated by the safety evaluation index calculation unit 42, are displayed on the display unit 34 of the mobile information terminal 3A under the control of the display control unit 33. Further, the external monitor data generation unit 36 performs various processes on the safety evaluation index calculated by the safety evaluation index calculation unit 42 under the control of the main body control unit 38A. Then, the safety evaluation index is wirelessly transmitted as the external monitor data following the display format for the external monitor 4 to the external monitor 4 through the terminal-side wireless communication unit 32. The safety evaluation index wirelessly transmitted to the external monitor 4 is displayed on the external monitor 4.

Here, it is desirable that the safety evaluation index is always displayed on the display unit 34 of the mobile information terminal 3A while a diagnosis using the ultrasound probe 2 is performed. In this case, the safety evaluation index may be displayed on the display unit 34 together with the terminal ultrasound image or the operation image CS1. In this configuration, even in a case in which the wireless communication state between the mobile information terminal 3A and the external monitor 4 deteriorates, the user can check at least the value of the safety evaluation index displayed on the display unit 34 of the mobile information terminal 3A to understand the influence of the ultrasonic waves transmitted from the transducer array 11 on the inside of the subject.

As described above, according to the ultrasound system of Embodiment 2, the safety evaluation index calculation unit 42 of the terminal-side processor 41A calculates the safety evaluation indices, such as the MI value and the TI value, and the calculated safety evaluation indices are displayed on the display unit 34 of the mobile information terminal 3A and the external monitor 4. Therefore, the user can check the safety evaluation indices displayed on the display unit 34 of the mobile information terminal 3A and the external monitor 4 to understand the influence of the ultrasonic waves transmitted from the transducer array 11 on the inside of the subject. In addition, the safety evaluation indices calculated by the safety evaluation index calculation unit 42 are always displayed on the display unit 34 of the mobile information terminal 3A. Therefore, even in a case in which the wireless communication state between the mobile information terminal 3A and the external monitor 4 deteriorates, the user can check the safety evaluation indices.

Embodiment 3

Figure 7:
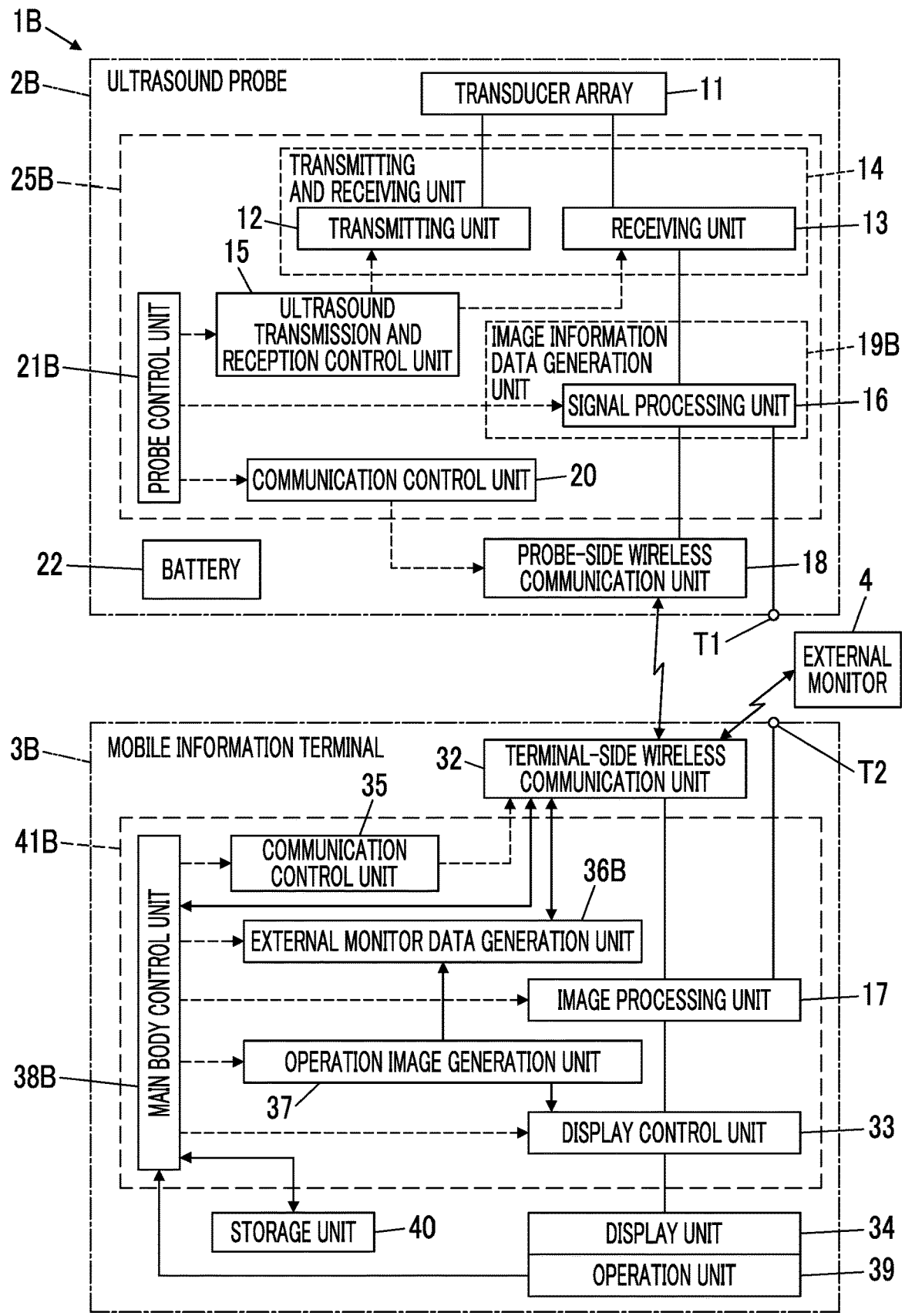
FIG. 7 is a block diagram illustrating a configuration of an ultrasound system according to Embodiment 3 of the invention.

FIG. 7 illustrates the configuration of an ultrasound system 1B according to Embodiment 3. The ultrasound system 1B comprises an ultrasound probe 2B, a mobile information terminal 3B, and the external monitor 4 that is the same as the external monitor 4 in Embodiment 1 illustrated in FIG. 1. The ultrasound probe 2B and the mobile information terminal 3B are connected to each other by wireless communication, and the mobile information terminal 3B and the external monitor 4 are connected to each other by wireless communication.

As illustrated in FIG. 7, the ultrasound probe 2B according to Embodiment 3 is different from the ultrasound probe 2 according to Embodiment 1 illustrated in FIG. 1 in that the image processing unit 17 is removed and a probe control unit 21B is provided instead of the probe control unit 21.

In the ultrasound probe 2B, the probe-side wireless communication unit 18 and the probe-side connection terminal T1 are directly connected to the signal processing unit 16, and an image information data generation unit 19B is configured by the signal processing unit 16. The probe control unit 21B is connected to the transmitting unit 12, the receiving unit 13, the ultrasound transmission and reception control unit 15, the signal processing unit 16, and the communication control unit 20. Further, a probe-side processor 25B is configured by the transmitting and receiving unit 14, the ultrasound transmission and reception control unit 15, the signal processing unit 16, the communication control unit 20, and the probe control unit 21B.

The mobile information terminal 3B according to Embodiment 3 is different from the mobile information terminal 3 according to Embodiment 1 illustrated in FIG. 1 in that it comprises the image processing unit 17 between the terminal-side wireless communication unit 32 and the display control unit 33, comprises an external monitor data generation unit 36B instead of the external monitor data generation unit 36, and further comprises a main body control unit 38B instead of the main body control unit 38.

In the mobile information terminal 3B, the image processing unit 17 is connected to the terminal-side wireless communication unit 32, and the display control unit 33 is connected to the image processing unit 17. The image processing unit 17 is also connected to the terminal-side connection terminal T2. The external monitor data generation unit 36B is connected to the terminal-side wireless communication unit 32, and the operation image generation unit 37 is connected to the external monitor data generation unit 36B. The main body control unit 38B is connected to the image processing unit 17, the display control unit 33, the communication control unit 35, the external monitor data generation unit 36B, and the operation image generation unit 37. Further, a terminal-side processor 41B is configured by the image processing unit 17, the display control unit 33, the communication control unit 35, the external monitor data generation unit 36B, the operation image generation unit 37, and the main body control unit 38B.

The signal processing unit 16 of the image information data generation unit 19B corrects the attenuation of the sound ray signal generated by the beam former 28 of the receiving unit 13 caused by a propagation distance according to the depth of the position where the ultrasonic waves are reflected and performs the envelope detection process on the sound ray signal to generate, as image information data, a signal that is tomographic image information related to the tissues in the subject.

The probe-side wireless communication unit 18 of the ultrasound probe 2B modulates a carrier on the basis of the signal generated by the signal processing unit 16 of the image information data generation unit 19B to generate a transmission signal indicating the image information data and wirelessly transmits the generated transmission signal to the terminal-side wireless communication unit 32 of the mobile information terminal 3B.

The terminal-side wireless communication unit 32 of the mobile information terminal 3B demodulates the transmission signal wirelessly transmitted from the ultrasound probe 2B to acquire the signal generated by the signal processing unit 16 of the image information data generation unit 19B and transmits the signal to the image processing unit 17 of the terminal-side processor 41B and the external monitor data generation unit 36B.

The image processing unit 17 of the terminal-side processor 41B raster-converts the signal transmitted from the terminal-side wireless communication unit 32 into an image signal following the general television signal scanning method and performs various types of necessary image processing, such as brightness correction, gradation correction, sharpness correction, image size correction, refresh rate correction, scanning frequency correction, and color correction following the display format for the display unit 34 of the mobile information terminal 3, on the generated image signal to generate an ultrasound image signal for the mobile information terminal 3B.

The ultrasound image signal generated by the image processing unit 17 is displayed on the display unit 34 as a terminal ultrasound image following the display format for the display unit 34 of the mobile information terminal 3B under the control of the display control unit 33.

The external monitor data generation unit 36B of the terminal-side processor 41B raster-converts the signal transmitted from the terminal-side wireless communication unit 32 into an image signal following the general television signal scanning method and performs various types of necessary image processing, such as brightness correction, gradation correction, sharpness correction, image size correction, refresh rate correction, scanning frequency correction, and color correction following the display format for the external monitor 4, on the generated image signal to generate an ultrasound image signal for the external monitor 4 as external monitor data.

Further, the external monitor data generation unit 36B performs various types of necessary image processing following the display format for the external monitor 4 on the operation image CS1 generated by the operation image generation unit 37 to generate data corresponding to the external monitor operation image CS2 as the external monitor data.

As such, since data corresponding to the image to be displayed on the display unit 34 and the external monitor 4 is generated in the mobile information terminal 3B, the user can use a general-purpose monitor device as the external monitor 4.

For example, the external monitor data including the ultrasound image signal for the external monitor 4 and the data corresponding to the external monitor operation image CS2 generated by the external monitor data generation unit 36B is wirelessly transmitted to the external monitor 4 through the terminal-side wireless communication unit 32 on the basis of the input operation of the user through the touch sensor of the operation unit 39 of the mobile information terminal 3B under the control of the communication control unit 35 and the main body control unit 38B. For example, the external monitor data wirelessly transmitted from the terminal-side wireless communication unit 32 to the external monitor 4 in this way is displayed as the external monitor ultrasound image UE and the external monitor operation image CS2 on the external monitor 4 as illustrated in FIG. 4.

As such, in a case in which the user performs an input operation through the touch sensor of the operation unit 39 of the mobile information terminal 3B with the external monitor ultrasound image UE and the external monitor operation image CS2 displayed on the external monitor 4, the operation related to display on the external monitor 4 is performed.

As described above, even in a case in which the image processing unit 17 is not provided in the ultrasound probe 2B, but is provided in the mobile information terminal 3B as in the ultrasound system 1B according to Embodiment 3, similarly to the ultrasound system 1 according to Embodiment 1, the external monitor data to be displayed on the external monitor 4 is generated in the mobile information terminal 3B, and the external monitor ultrasound image UE and the external monitor operation image CS2 are displayed on the external monitor 4 on the basis of the external monitor data. In addition, the user operates the ultrasound system 1B through the operation unit 39 of the mobile information terminal 3B. Therefore, it is possible to improve convenience in ultrasound diagnosis while facilitating the observation of the ultrasound image and an input operation for ultrasound diagnosis.

In the above-described Embodiments 1 and 2, the ultrasound image signal which has been subjected to the attenuation correction and the envelope detection process by the signal processing unit 16 of the image information data generation unit 19 and then subjected to raster conversion by the image processing unit 17 is transmitted as the image information data from the probe-side wireless communication unit 18 to the mobile information terminal 3 and the mobile information terminal 3A. In addition, in Embodiment 3, the signal subjected to the attenuation correction and the envelope detection process by the signal processing unit 16 of the image information data generation unit 19B is transmitted as the image information data from the probe-side wireless communication unit 18 to the mobile information terminal 3B. However, it is preferable that the image information data transmitted from the ultrasound probe 2 to the mobile information terminals 3 and 3A and the image information data transmitted from the ultrasound probe 2B to the mobile information terminal 3B are signals after detection. However, the image information data is not limited to the signal after detection.

EXPLANATION OF REFERENCES 1, 1B: ultrasound system
2, 2B: ultrasound probe
3, 3A, 3B: mobile information terminal
4: external monitor
11: transducer array
12: transmitting unit
13: receiving unit
14: transmitting and receiving unit
15: ultrasound transmission and reception control unit
16: signal processing unit
17: image processing unit
18: probe-side wireless communication unit
19, 19B: image information data generation unit
20, 35: communication control unit
21, 21B: probe control unit
22: battery
25, 25B: probe-side processor
26: amplification unit
27: AD conversion unit
28: beam former
32: terminal-side wireless communication unit
33: display control unit
34: display unit
36, 36B: external monitor data generation unit
37: operation image generation unit
38, 38A, and 38B: main body control unit
39: operation unit
40: storage unit
41, 41A, 41B: terminal-side processor
42: safety evaluation index calculation unit.
B1: B-mode button
B2: CD-mode button
B3: PW-mode button
B4: M-mode button
B5: scroll button
B6: freeze button
B7: storage button
CC: connection cable
CS1: operation image
CS2: external monitor operation image
SD1: terminal-side display screen
SD2: external-monitor-side display screen
T1: probe-side connection terminal
T2: terminal-side connection terminal
UE: external monitor ultrasound image

What is claimed is:

1. An ultrasound system in which a mobile information terminal is connected to an ultrasound probe and an external monitor,
    wherein the ultrasound probe includes:
    a transducer array;
    a processor that transmits ultrasonic waves from the transducer array and generates a sound ray signal on the basis of a reception signal acquired by the transducer array, and generates image information data on the basis of the sound ray signal; and
    a wireless communication unit that wirelessly transmits the image information data to the mobile information terminal,
    the mobile information terminal includes:
    a display unit;
    an operation unit that includes a touch sensor disposed so as to be superimposed on the display unit and is used by a user to perform an input operation;
    a processor that generates an operation image which is displayed on the display unit and is used by the user to perform the input operation through the touch sensor, generates external monitor data having a display format for the external monitor on the basis of the image information data wirelessly transmitted from the ultrasound probe, and detects whether or not the mobile information terminal and the external monitor are connected to each other; and
    a wireless communication unit that wirelessly transmits the external monitor data generated by the processor of the mobile information terminal to the external monitor, and
    the external monitor displays an external monitor ultrasound image on the basis of the external monitor data wirelessly transmitted from the mobile information terminal, and
    only while that the mobile information terminal and the external monitor are not connected each other is being detected and the external monitor ultrasound image is not being displayed on the external monitor, the display unit displays both of the operation image and a terminal ultrasound image based on the image information data generated by the processor of the ultrasound probe.

2. The ultrasound system according to claim 1,
wherein the external monitor data includes data corresponding to the external monitor ultrasound image and the operation image generated by the processor of the mobile information terminal, and
the external monitor displays the external monitor ultrasound image and an external monitor operation image that is the same as the operation image displayed on the display unit of the mobile information terminal on the basis of the external monitor data.

3. The ultrasound system according to claim 2,
wherein the external monitor has a display screen having a first size,
the display unit of the mobile information terminal has a display screen having a second size that is smaller than the first size,
the external monitor operation image has a size equal to the second size of the display screen of the mobile information terminal, and
the external monitor ultrasound image has a third size that is smaller than the first size and is larger than the second size.

4. The ultrasound system according to claim 1,
wherein a wireless communication method between the mobile information terminal and the ultrasound probe is different from a wireless communication method between the mobile information terminal and the external monitor.

5. The ultrasound system according to claim 2,
wherein a wireless communication method between the mobile information terminal and the ultrasound probe is different from a wireless communication method between the mobile information terminal and the external monitor.

6. The ultrasound system according to claim 4,
wherein a frequency band in wireless communication between the mobile information terminal and the ultrasound probe is different from a frequency band in wireless communication between the mobile information terminal and the external monitor.

7. The ultrasound system according to claim 5,
wherein a frequency band in wireless communication between the mobile information terminal and the ultrasound probe is different from a frequency band in wireless communication between the mobile information terminal and the external monitor.

8. The ultrasound system according to claim 1,
wherein the mobile information terminal calculates a safety evaluation index on the basis of ultrasound transmission and reception conditions controlled by the processor of the ultrasound probe and displays the safety evaluation index on the display unit.

9. The ultrasound system according to claim 1,
wherein the image information data is a signal obtained by performing attenuation correction according to a depth of a reflection position of the ultrasonic waves and an envelope detection process on the sound ray signal generated by the processor of the ultrasound probe.

10. The ultrasound system according to claim 1,
wherein the image information data is an ultrasound image signal obtained by performing attenuation correction according to a reflection position of the ultrasonic waves and an envelope detection process on the sound ray signal generated by the processor of the ultrasound probe and converting the sound ray signal according to a predetermined image display method.

11. The ultrasound system according to claim 1,
wherein the processor of the ultrasound probe directs the transducer array to transmit the ultrasonic waves, and generates the sound ray signal on the basis of the reception signal acquired by the transducer array.

12. A method for controlling an ultrasound system in which a mobile information terminal is connected to an ultrasound probe and an external monitor, the method comprising:
generating a sound ray signal by directing a transducer array of the ultrasound probe to transmit and receive ultrasonic waves on the basis of an input operation through an operation unit of the mobile information terminal;
generating image information data on the basis of the generated sound ray signal;
wirelessly transmitting the generated image information data from the ultrasound probe to the mobile information terminal;
generating an operation image used by a user to perform an input operation;
displaying the operation image on a display unit of the mobile information terminal;
generating external monitor data having a display format for the external monitor on the basis of the image information data wirelessly transmitted from the ultrasound probe;
detecting whether or not the mobile information terminal and the external monitor are connected to each other;
wirelessly transmitting the generated external monitor data from the mobile information terminal to the external monitor;
displaying an external monitor ultrasound image on the external monitor on the basis of the external monitor data; and
only while that the mobile information terminal and the external monitor are not connected each other is being detected and the external monitor ultrasound image is not being displayed on the external monitor, displaying both of the operation image and a terminal ultrasound image based on the image information data on the display unit.

* * * * *